United States Patent [19]

Spenney

[11] 4,207,308

[45] Jun. 10, 1980

[54] PROCESS FOR PURIFYING IODINATED BILE ACID CONJUGATES

[75] Inventor: Jerry G. Spenney, Birmingham, Ala.

[73] Assignee: The United States of America as represented by the Administrator of Veterans Affairs, Washington, D.C.

[21] Appl. No.: 805,960

[22] Filed: Jun. 13, 1977

Related U.S. Application Data

[63] Continuation-in-part of Ser. No. 719,753, Sep. 2, 1976, abandoned.

[51] Int. Cl.$^2$ ..................... A61K 29/00; A61K 43/00
[52] U.S. Cl. ..................... 424/1; 260/397.1; 260/239.57; 260/112 R; 424/106; 424/242
[58] Field of Search ............ 260/397.1, 397.5, 239.55, 260/239.57, 112 R; 424/1, 9, 1.5, 106, 242

[56] References Cited

U.S. PATENT DOCUMENTS 3,855,208   12/1974   Rutner et al. ................... 260/239.57

OTHER PUBLICATIONS

Demers et al., Clin. Chem., vol. 22, No. 5, May 1976, pp. 602-606.
Spenney et al., Gastroenterology, vol. 69, p. A68/868, Sep. 23, 1975.
Bolton et al., Biochem. J., vol. 133, 1973, pp. 529-539.
Spenney et al., Gastroenterology, vol. 72, No. 2, 1977, pp. 305-311.

*Primary Examiner*—Benjamin R. Padgett
*Assistant Examiner*—Christine M. Nucker
*Attorney, Agent, or Firm*—Leon Zitver; Norman J. Latker; Thomas G. Ferris

[57] ABSTRACT

Iodinatable bile salt derivatives are obtained by providing bile salts and their glycine and taurine conjugates with iodinatable groups. The radioiodinated compounds are useful in the radioimmunoassay of bile salts and in physiological studies. The preferred compound is cholylglycylhistamine. The synthesis of radioiodinated conjugates and their purification by extraction and silica gel chromatography are described.

19 Claims, 10 Drawing Figures

PROCESS FOR PURIFYING IODINATED BILE ACID CONJUGATES

This application is a continuation-in-part of my application, Ser. No. 719,753, filed Sept. 2, 1976, abandoned.

FIELD OF THE INVENTION

This invention relates to a new group of bile salt derivatives which have the common property that they can be iodinated using either stable or unstable isotopes of iodine. The invention further relates to radioiodinated bile salt derivatives, their preparation and purification, and their application to bile salt radioimmunoassays, hepatic-uptake and excretion measurements and hepatic scintigraphy.

BACKGROUND OF THE INVENTION

Recent publications for several laboratories have emphasized the potential sensitivity of serum bile salt measurements in detecting liver disease. Because of technical complexity these assays have been restricted to a few laboratories.

Assay of total and individual bile salts in serum by thin layer or gas/liquid chromatography has been in limited use in clinical research for several years. Recently development of fluorimetric assays using the 3-α and 7-α-hydroxysteroid dehydrogenase enzymes from microorganisms has increased the sensitivity to levels at which serum assays are feasible. The recent availability of a purified enzyme (Sterognost 3-α) may increase the specificity of this assay. Nonetheless extraction is still required before assay.

Recently, radioimmunoassay of various bile salts has simplified the assay procedure and allowed measurement of individual bile salts in serum from normal individuals. These radioimmunoassays are based on tritiated bile salts or $^{35}S$ (in the case of sulfated bile salts), these being β-emitting tracers. Wide clinical usage has not yet been achieved perhaps because (a) clinical bile salt measurements are of uncertain value; (b) equipment required (liquid scintillation counter) for tritium based RIA are cumbersome, expensive and not widely available; (c) the expense of a tritium based assay (equipment, scintillation fluor and counting vials) cannot be justified in many clinical labs; and (d) low specific activity tracers and low antibody titers make antibody supply uncertain. Uncertainty of the clinical value of serum bile salt measurement is being clarified and clinical studies utilizing these assays will increase in frequency. Already it has been shown that serum bile salt measurements were the earliest predictor of relapse in chronic active hepatitis. The remaining problems would be largely obviated by a high specific activity tracer such as $^{125}I$, a γ-emitting radionuclide. The common bile salts, however, do not have a site which can be iodinated.

Various compounds which have no site for iodination—adrenal steroids, testosterone, estrogens and cyclic nucleotides—have been chemically modified by addition of histamine, tyrosine, tyrosine methyl ester, or phenylpropionic acid which can be iodinated. These derivatives have provided $^{125}I$ based immunoassays for these compounds.

The specific activity of radioiodinated bile salts would approach 2000 Ci/mMole as opposed to 3.5 Ci/nM for $^3H$ tracers. The increased specific activity would allow increased sensitivity and increased antibody titers and could be quantitated using the γ-spectrometer instead of liquid scintillation spectrometers. In addition the γ-emitting derivative, if physiologically active, could be useful for physiologic studies of transport or absorption of bile salts. Blood clearance of bile salts and hepatic uptake and excretion could be measured; hepatic and biliary and intestinal scintigraphy or quantitative scintigraphy could be performed and ileal absorptive function could be quantitated. The common bile salts, however, have no group which can be iodinated easily.

It is an object of this invention to provide bile salt derivatives which can be iodinated easily.

A further object of this invention is to provide radioiodinated bile salt derivatives.

An additional object of this invention is to provide methods for purifying such derivatives.

Other objects of the invention are to use such radioiodinated bile salt derivatives in radioimmunoassays, the measurement of hepatic uptake and excretion, and scintigraphy.

Other objects of this invention will be apparent hereinafter.

SUMMARY OF THE INVENTION

It has now been found that the objects of the invention may be accomplished by providing bile acids and their amino acid and diamine conjugates with iodinatable groups. More particularly, the bile acids and conjugates contemplated are cholic acid, chenodeoxycholic acid, deoxycholic acid and lithocholic acid and their glycine and taurine conjugates bonded in a peptide (amide) bond, as well as their conjugates with other amino acids and diamines, as illustrated by the following formula:

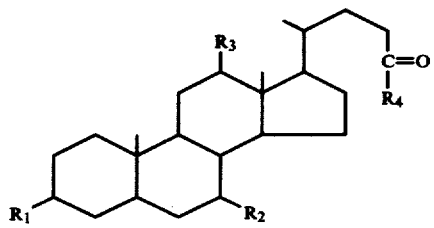

$R_1$, $R_2$ and $R_3$ may be either —OH or —H within the limits of the following table:

|  | $R_1$ | $R_2$ | $R_3$ |
|---|---|---|---|
| Cholic acid | —OH | —OH | —OH |
| Chenodeoxycholic acid | —OH | —OH | —H |
| Deoxycholic acid | —OH | —H | —OH |
| Lithocholic acid | —OH | —H | —H |

$R_4$ may be —OH, or glycine or taurine bonded in an amide (peptide) bond, or another amino acid or a diamine similarly bonded.

Contemplated as the iodinatable groups are tyrosine and tyrosine ester groups, histidine and histidine ester groups, tyramine, histamine, phenylpropionic acid, phenylalanine and phenylalanine ester groups, and tryptophane and tryptophane ester groups.

These groups can be attached at the $C_{24}$ carboxyl group of the bile salt or the carboxyl group of glycine conjugated bile salts. In addition they can be attached either directly or through a bridging group such as succinic acid or other dicarboxylic acids to the 3-α-hydroxyl group of the bile salt.

Illustrative of the foregoing are:

a. Derivatives using a diamine:

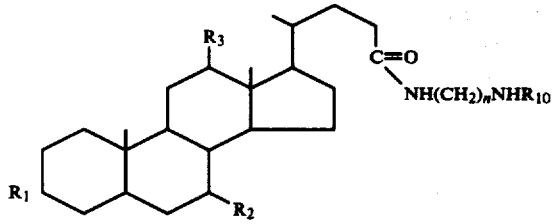

where $n \geq 2$ and $R_{10}$ is tyrosine, histidine, phenylalanine, tryptophane or phenylpropionic acid, in which the amino group (in the case of the first 4) is primary, secondary or tertiary, $R_{10}$ being bonded in an amide bond.

b. The derivatives at the $C_{24}$ carboxyl group of the bile salts:

e.g.

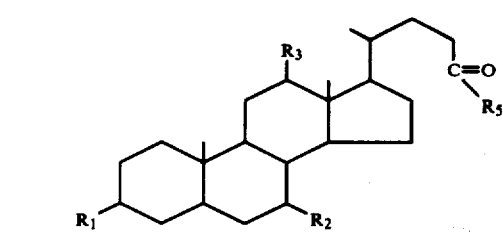

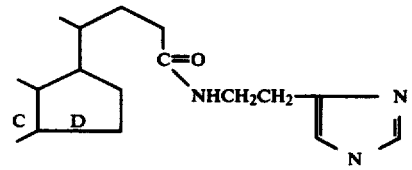

steroid rings
of bile salts $R_5$ may be tyrosine, a tyrosine ester, histidine, a histidine ester, phenylalanine, a phenylalanine ester, tryptophane, a tryptophane ester, tyramine, or histamine bonded in an amide bond. Lithocholylhistamine and cholyltyrosine are specific examples.

c. Derivatives at the carboxyl group of glycine conjugates or bile salts conjugated with other amino acids. Glycine conjugate is used as an example.

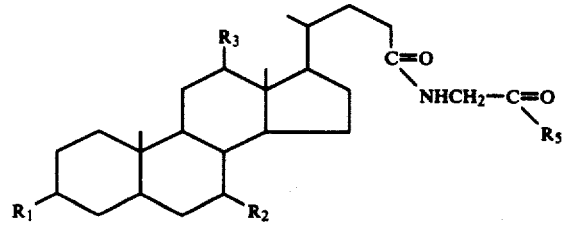

$R_5$ is as above described and is similarly bonded.

Cholylglycylhistamine and deoxycholylglycylhistidine are specific examples.

d. Derivatives at the 3-α-hydroxyl group.

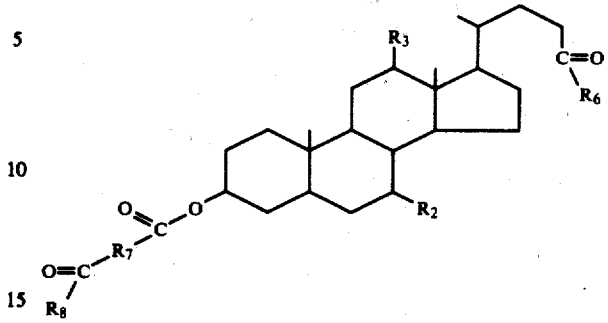

$R_6$ is —OH or an alcohol bonded in an ester bond or a glycine ester (e.g. methyl ester) or taurine or ester of other amino carboxylic acids, the amino acids being bonded in an amide bond. $R_7$ is $-(CH_2)_n-$ where n is 1 or more. $R_8$ is the same as $R_5$.

e. Additional derivatives at the 3-α-hydroxyl group.

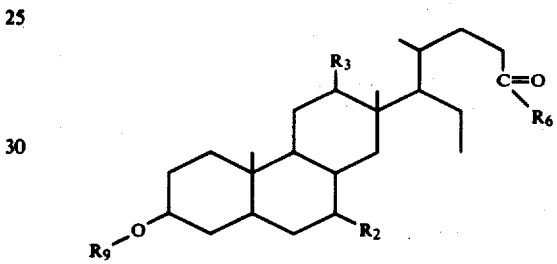

$R_9$ is the same as $R_5$ except for histamine and tyramine and is bonded in an ester bond, and in which the amino group may be primary, secondary or tertiary.

The esters referred to in the above illustrations are typically alkyl esters, such as the methyl esters.

The compounds above described wherein the iodinatable group is attached in an amide bond may be prepared by the carbodiimide method or the N-hydroxysuccinimide activated ester method. The compounds wherein the iodinatable group is attached in an ester bond may be prepared by standard esterification procedure, such as heating with anhydrous acids. Iodination is accomplished by the chloramine-T method or other standard methods. Purification is by extraction and silica gel chromatography.

The above described bile salt derivatives are useful in the radioimmunoassay of bile salts, physiological research and clinical studies such as bile salt clearance rates; measurement of ileal absorption, hepatic uptake and excretion; hepatic, biliary and intestinal scintigraphy; and quantitative scintigraphy.

The novel compounds having amine groups may be crystallized and stored in the form of the acid addition salts, such as the hydrochlorides and phosphates. The novel compounds having free carboxyl and sulfonic acid groups can similarly be isolated as the base addition salts, such as the sodium, potassium, ammonium or dicyclohexylamine salts.

Particularly preferred is the compound cholylglycylhistamine, having, in its hydrochloride form, the following structural formula:

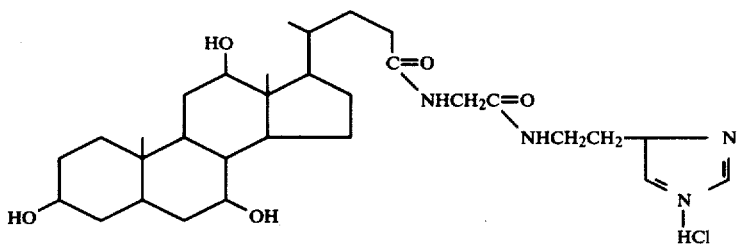

The preferred method of obtaining the radioiodinated derivative is by iodination using $Na^{125}I$ and chloramine-T. The products are largely mono-iodinated but may contain some di-iodinated products.

Although the preferred iodine isotope is $^{125}I$, $^{131}I$ and $^{123}I$ may also be employed. $^{131}I$, although having a shorter half life and less favorable energy spectrum than $^{125}I$, is useful where high energy radiation is needed such as in scintigraphy. $^{123}I$ also has advantages in scintigraphy.

DETAILED DESCRIPTION OF THE INVENTION

Figure 1:
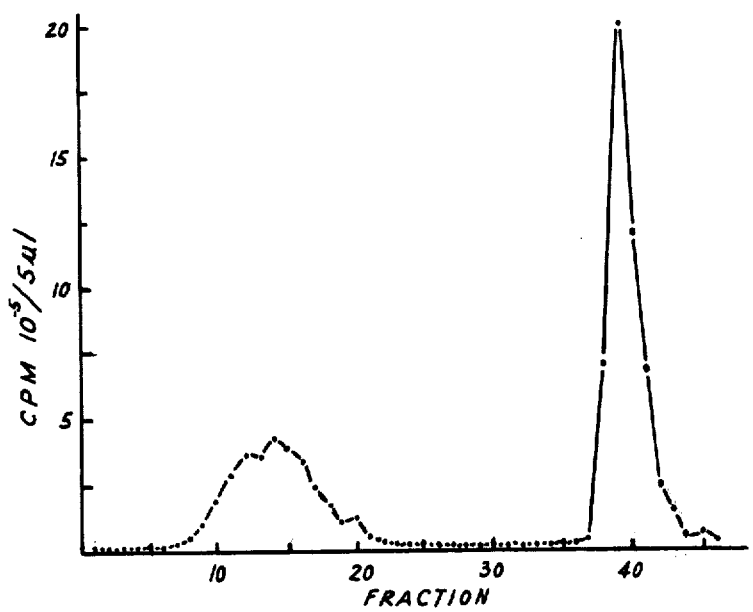
FIG. 1 is a graph showing the fractionation obtained by eluting the iodinated product obtained in Example 2.

In carrying out the iodination reaction, molar proportions of bile acid conjugate to NaI ranging from 1:1 to 100:1, or even higher, may be employed. In the case of $^{125}I$, 1–2 mCi (0.5–1 nMoles) $Na^{125}I$ and about 35 μg chloramine-T are employed and the reaction is strongly buffered at pH 7.4 using 0.5 M $Na^+$ or $K^+$ phosphate buffer. The reaction is initiated by adding the chloramine-T and proceeds with stirring for about 30–60 seconds. The reaction is terminated by adding sodium metabisulfite, typically about 250 μg. The reaction mixture is diluted to about 2 ml with 10 mM of the above described phosphate buffer.

The preferred first step in purification is chromatography on a resin of the type used in such procedures. Polystyrene based chromatographic materials, generally, including those of the styrene-divinyl benzene copolymer type, such as Amberlite XAD-2 and the Dowex resins, may suitably be used, as well as resins of the acrylic polymer type such as Amberlite XAD-7. Ion exchange resins of the Dowex or Amberlite series or cellulose series may be employed. The unreacted bile acid conjugate and the iodinated conjugate are adsorbed onto the resin while free iodine and other reaction products are voided by washing the column with 10 mM phosphate buffer, suitably pH 7.4, and water. Fractions are collected and counted in a γ-spectrometer. When the free radioiodine peak has been eluted, the mixture of unreacted and iodinated conjugate is eluted, preferably with methanol or ethanol, although other solvents, such as acetone, ether or ethyl acetate may be employed. Aliquots of each eluted fraction are counted in the γ-spectrometer and the fractions containing the unreacted plus the iodinated conjugate are pooled. In the case of $^{131}I$, this pooled material may be used for scintigraphy.

Use of molar proportions of conjugate to NaI ranging from 50:1 to 100:1 and a reaction time of 60 seconds results in incorporation of 70% to nearly 100% of the iodine. For this excellent incorporation, the price paid is low specific activity. Whereas (in the case of cholylglycyl-$^{125}I$-histamine) the specific activity of the starting $Na^{125}I$ is 2125 Ci/m Mole, the specific activity of the $CGH + CGH^{125}I$ at ths stage is about 21.25 Ci/m Mole. Material of this specific activity is useful for scintigraphy, especially where $^{131}I$ is employed, but before it can be optimally employed for radioimmunoassay, it is important that it be further purified.

To obtain an essentially carrier free product (free of unlabelled bile acid conjugate), the pooled unreacted plus iodinated material, obtained as above described, is concentrated by evaporation, suitably to 100 μl or less, with a stream of air or inert gas (nitrogen, argon, helium, xenon, etc.). The concentrated material is subjected to thin layer chromatography, silica gel chromatography sheets being suitably employed. The material is applied by streaking or spotting in the usual manner. It is then air dried to remove the solvent and developed in a solvent. In the case of iodinated cationic bile acid conjugates, solvents containing a nitrogen base have been found to give good separations. The nitrogen base employed is preferably triethylamine, but other primary, secondary and tertiary amines, as well as ammonium hydroxide and hydroxylamine may be employed. Among the amines useful for the purpose are, in addition to triethylamine, other alkyl amines such as trimethylamine, tripropylamine and tributylamine, cycloalkylamines such as dicyclohexylamine, arylamines such as aniline, and heterocyclic amines such as pyridine. In addition to the nitrogen base, the solvent should suitably contain a lower alkyl ester of a lower alkanoic acid, the lower alkyl group being defined as containing 1 to 6 carbon atoms and the ester containing in all up to 8 carbon atoms. Other components of the solvent may include benzene or a lower homologue thereof, a lower alkanol, a lower alkanone and a di-lower alkyl ether, wherein the alkyl moieties are as defined previously and in the case of the ether may be the same or different. The preferred ranges of proportions of these compounds are: nitrogen base, 5–20%; lower alkyl ester of lower alkanoic acid, 20–80%; the other components, used alone or in combination, 0–75%. A solvent containing one of the above mentioned nitrogen bases, a lower alkanol, ethyl acetate and benzene has been found to be suitable. A very suitable solvent is composed of 25 parts by volume of the lower alkanol (preferably methanol or ethanol), 10 parts by volume of the nitrogen base (preferably triethylamine) and 75 parts by volume of a mixture of ethylacetate and benzene, each of which is used in an amount ranging from 25 to 50 parts by volume.

In the case of iodinated anionic bile acid conjugates (e.g. those containing a free acid radial) an acidic solvent system may be employed. Such a system may be similar to those described above for use with cationic bile acid conjugates, with the exception that a weak acid such as acetic acid is employed instead of nitrogen base. A solvent containing 40% ethyl acetate, 40% benzene, 10% methane and 10% acetic acid (by volume) is suitable. In procedures using these systems, a band of uniodinated conjugate migrates to a position beyond a band of iodinated conjugate.

Among the thin layer chromatographic materials which may be employed, in addition to silica gel, are alumina, kieselguhr and other coating materials, as described on pp. 29–34 of Stahl, "Thin Layer Chromatography," (Springer Verlag, New York 1965). The solvent may be caused to move, depending on the apparatus employed, in an ascending, descending or horizontal manner, as known in the art and described by Stahl, although the ascending method is preferred. In any case, the labelled compound migrates to a position on the chromatography sheet different from that of the unlabelled compound.

To aid in localizing the radiolabelled compound on the chromatography sheet, the following procedure (using $^{125}$I-CGH as illustrative) may be employed:

The concentrated material is streaked along the origin of a silica gel chromatography sheet using a fine glass capillary. Tracks at each side of the sheet are made for unlabelled CGH.

After the chromatogram has run and been dried, suitably by air drying, to remove the solvent, $^{125}$I is spotted in corners and/or elsewhere in the chromatogram to aid orientation. The chromatogram is placed over a sheet of X-ray film in a cardboard cassette for 10–30 minutes depending on the amount of radioactivity used in the reaction.

The principal exposure on the X-ray film underlies the position of the $^{125}$I-CGH. After exposure, the chromatography sheet containing the unlabelled CGH are sprayed with Pauley's reagent. The portion of the chromatogram containing the iodinated bile salt is protected from the spray. The X-ray film is developed. The chromatogram is positioned over the autoradiograph to localize the labelled compound on the chromatography sheet. The $^{125}$I spots are used to assist in positioning the chromatogram properly. The location of the iodinated CGH is marked on the chromatogram being careful not to include the unlabelled material (localized by the unlabelled material run in the outside tracks of the chromatogram).

Another method of localizing the labelled compound not requiring the use of X-ray film involves protecting the upper portions of the chromatogram and spraying the lower portion with Pauley's reagent. The level of spraying is slowly raised until the CGH is visualized. The radiolabelled material is just above this.

After the chromatogram has dried, the area of the chromatogram containing the $^{125}$I-CGH is cut out or scraped off, and the $^{125}$I-CGH eluted with a suitable solvent, such as ethanol, slowly dripped on the chromatogram. Any silica gel which washes off may be removed by centrifugation or millipore filtration. For use in acute animal experiments or immunoassays, the $^{125}$I-CGH is diluted to 100–250 ml with 10 mM Na$^+$ or K$^+$ phosphate buffer pH 7.4 containing bovine gamma globulin (1 mg/ml). The volume used depends on the concentration ($\mu$Ci/ml) desired.

For pharmaceutical uses in man, pharmaceutically acceptable carriers would be employed instead of one containing bovine gamma globulin.

The following examples illustrate but do not limit the invention. All chemicals used were reagent grade or the best grade available. Cholylglycine for immunization and bile salts for standard curves were purchased from Supelco. Cholylglycine for synthesis was purchased from Sigma. 1-Ethyl-3-(3-dimethylaminopropyl)carbodiimide-HCl (EDC), histamine dihydrochloride, N-hydroxysuccinimide and triethylamine were purchased from Aldrich. $^3$H-cholylglycine was purchased from New England Nuclear, and Na$^{125}$I and Na$^{131}$I from Amersham Searle and New England Nuclear.

EXAMPLE 1

Synthesis of Cholylglycylhistamine

Ten mMoles of cholylglycine and 10 mMoles of N-hydroxysuccinimide were dissolved in 75 ml of N,N-dimethylformamide. Ten mMoles of EDC were added and the mixture was stirred at 23° C. for 1.5 hours. Ten mMoles of histamine dihydrochloride and 10 mMoles of triethylamine were suspended in 25 ml of N,N-dimethylformamide and added to the activated ester formed above. The reaction was allowed to continue for 2 hours. The reaction was terminated by addition of an equal volume of H$_2$O and adjusting the pH to 10–11 with NaOH. After 60 minutes the pH was adjusted to 5 with HCl and the solution was poured over a Dowex 50W×8 cation exchange column containing 20 gm of resin which was previously washed with ethanol and benzene and then equilibrated with N,N-dimethylformamide:H$_2$O (1:1) adjusted to pH 5.0. After the sample absorbed, the column was washed with 50 ml of N,N-dimethylformamide:H$_2$O (9:1) and then with 100 ml absolute ethanol. The cholylglycylhistamine was eluted with ethanol: NH$_3$ (85:15). Three milliliter aliquots were collected and every fifth tube was tested for bile salt and histamine by spot testing 10 $\mu$l samples on silica gel plates. Bile salt was visualized by spraying with 15% phosphomolybdic acid in ethanol and heating. Histamine was visualized by spraying with Pauley's reagent (diazotized sulfanilic acid) as described by Stahl in "Thin Layer Chromatography," p. 899 (Springer Verlag, New York, 1969).

Fractions containing both bile salt and histamine were chromatographed to exclude free histamine. The samples containing cholylglycylhistamine were pooled and evaporated under reduced pressure using a rotary evaporator. The cholylglycylhistamine was a light golden oil. The cholylglycylhistamine was dried 18 hours in a vacuum, dissolved in absolute ethanol and crystallized as the hydrochloride salt by addition of HCl. The crystals were collected by filtration, washed with a small volume of ethanol, and dried under a vacuum. The melting point of the crystals was 191°-194° C.

Completion of the reaction leading to the activated ester can be checked using either a mixture of ethyl acetate, benzene, methanol and acetic acid (40:40:10:10) or a mixture of ethyl acetate, benzene, methanol and triethylamine (50:25:25:10) as solvent. The reaction leading to cholylglycylhistamine can be checked by thin layer chromatography on two separate sheets. One sheet is stained for bile salts with 15% phosphomolybdic acid in ethanol and the other is developed with Pauley's reagent as described by Stahl. When the reaction is complete the free histamine spot should be faint or vanish while the free cholylglycine spot should vanish and a new cholylglycylhistamine spot should predominate.

ANALYSIS OF PRODUCT

The product was analyzed for cholate, glycine and histamine following hydrolysis at 110° C. in sealed, evacuated ampules. Samples were hydrolyzed in 6 N HCl for periods up to 120 hours while samples in 1.25 M NaOH were hydrolyzed for as long as 8 hours.

Hydrolysates were analyzed for cholate by the 3-α-hydroxysteroid dehydrogenase reaction as reported by Murphy et al in "J.Clin.Path.," Vol. 23, pp. 594–8 (1970). Glycine was assayed on a Durrum amino acid analyzer, and histamine was quantitated using the o-phthalaldehyde reaction as modified by Hakanson and Rönnberg ("Anal.Biochem.," Vol. 60, pp. 560–67 (1974)).

Hydrolysis at 110° C. in sealed evacuated ampules containing 6 N HCl was found to give low recoveries of cholic acid as measured by the 3-α-hydroxysteroid dehydrogenase reaction. The prolonged hydrolysis (80–120 hours) necessary for quantitative recovery of glycine may have accounted for the observed degradation of the steroid moiety, but glycine and histamine could be quantitatively recovered. To quantitate cholate, alkaline hydrolysis in 1.25 M NaOH for 1 hour at 110° C. in sealed, evacuated ampules was necessary; histamine could also be quantitated. Because of NaCl present following neutralization, amino acid analysis was not successful and glycine could not be measured. Table I gives the results of these combined analyses for cholate, glycine and histamine. The ratio (1:0.94:1.01) is felt to be within experimental error since all components could not be quantitated in a single hydrolysate. Thus the structure shown above is confirmed.

In Table I, the total is the theoretical amount taken for hydrolysis based on a molecular weight of 596.32. The calculated composition is based on the assay of hydrolysates; histamine is common to both hydrolysis techniques.

TABLE I

|  | Acid Hydrolysis (nMoles) | Alkaline Hydrolysis (nMoles) | Calculated Composition Moles |
|---|---|---|---|
| Total | 3120 | 1615 | 1 |
| Cholate | — | 1395 | 1 |

TABLE I-continued

|  | Acid Hydrolysis (nMoles) | Alkaline Hydrolysis (nMoles) | Calculated Composition Moles |
|---|---|---|---|
| Glycine | 3088 | — | 0.94 |
| Histamine | 3338 | 1403 | 1.01 |

EXAMPLE 2

Iodination of Cholylglycylhistamine

Fifty nMoles (10 μl) of cholylglycylhistamine were taken from a 20% ethanolic aqueous solution containing 5.0 μM/ml. 10 μl of 0.5 M phosphate buffer pH 7.4, 2 mCi (1 nMole) of Na$^{125}$I (about 2.5 μl), and 35 μg (10 μl) of chloramine-T in 0.5 M phosphate buffer pH 7.4 was added and the mixture was stirred on a magnetic stirrer for 30 seconds. 250 μg (100 μl) sodium metabisulfite was added to terminate the reaction. Two ml of 10 mM phosphate buffer pH 7.4 was added to the reaction mixture which was fractionated using an Amberlite XAD-2 column (0.7×3 cm, Brinkman Inst.) containing about 1 gm of resin. The column was eluted at 0.2 ml/minute and 0.2 ml fractions were collected. After the sample had adsorbed, the column was washed with 3 ml 10 mM PO$_4$ buffer pH 7.4 and then with distilled H$_2$O until the free $^{125}$I peak had been eluted. The iodinated cholylglycylhistamine was eluted with absolute ethanol. Iodinations done by this technique have a relatively low specific activity and should be purified further. Potassium was the metal cation used in the buffer but sodium or other cations may be used.

FIG. 1 shows the fractionation obtained by this technique. The first peak, eluted with aqueous buffer, represents free Na$^{125}$I and in this iodination accounted for about ¼ of the Na$^{125}$I. The second peak, eluted with ethanol or methanol, contains the mono- or di-iodo cholylglycylhistamine. To achieve 66% incorporation of $^{125}$I a large molar excess of cholylglycylhistamine was used; thus the iodinated product has low specific activity but the mono-iodinated derivative should have almost exclusively been formed.

EXAMPLE 3

Purification of Cholylglycyl-$^{125}$I-histamine

The cholylglycyl-$^{125}$I-histamine peak was pooled and evaporated to a volume of approximately 0.1 ml under a stream of dry nitrogen. The pool was applied to a silica gel chromatography sheet (Eastman Kodak) by streaking; in tracks on both sides of the plate 10 nMoles of authentic cholylglycylhistamine and a sample of the original pool were spotted. The chromatogram was developed using ethyl acetate:benzene:methanol:triethylamine (50:25:25:10). After the solvent ascended and the plate dried, Na$^{125}$I was spotted in 3 places and an autoradiograph was made by exposing X-ray film in a cardboard cassette for 10–30 minutes. The film was developed and the portions of the chromatogram on which the authentic cholylglycylhistamine was spotted were sprayed with Pauley's reagent. The chromatogram and autoradiograph were superimposed and the iodinated band which migrated 2 cm above the authentic cholylglycylhistamine spots was localized and cut or scraped from the chromatogram being careful not to include the non-iodinated material. The iodinated cholylglycylhistamine was eluted from the silica gel with absolute ethanol. This product may contain some disubstituted derivative but in most instances will be largely mono-iodinated.

Figure 2:
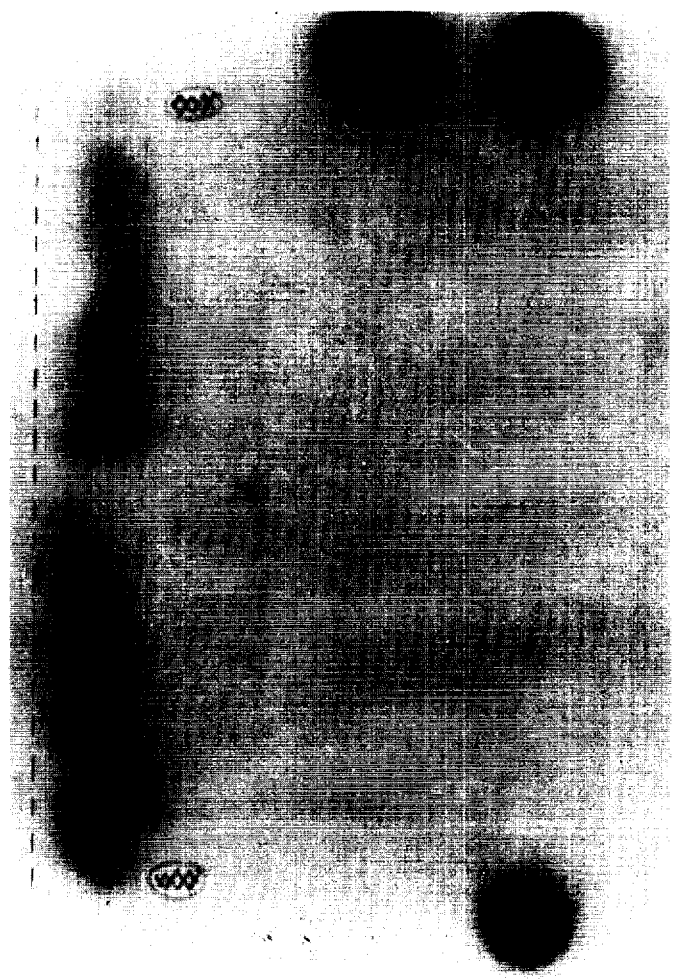
FIG. 2 is an autoradiograph prepared by the purification procedure of Example 3.

FIG. 2 shows an autoradiograph prepared in this way. The spots (cross hatched) indicating the non-iodinated authentic cholylglycylhistamine were drawn by superimposing the autoradiograph on the chromatogram. The clear separation of cholylglycylhistamine from cholylglycyl-$^{125}$I-histamine is shown. Cutting out the $^{125}$I area of the chromatogram and elution with 10 ml ethanol gave carrier-free cholylglycylhistamine. Elution was 99+% complete. The material was diluted to about 5 μCi/ml in 10 mM phosphate buffer pH 7.4 (as above described) containing 1 mg bovine gamma globulin/ml of solution. Cholylglycyl-$^{125}$I-histamine can be stored at −20° C. or −70° C. and in our experience has shown no deterioration (decreasing initial B/F or increasing non-specific binding) in storage for three half-lives (6 months).

The following table lists chromatographic solvent systems useful in the synthesis, iodination and/or analysis of cholylglycylhistamine by silica gel (Eastman Kodak) thin layer chromatography. Solvent system I is acidic, the others basic. In solvent system I, cholic acid has an $R_f$ of 0.7, cholylglycine an $R_f$ of 0.4 and cholylglycylhistamine does not move appreciably. In solvent system II cholylglycylhistamine has an $R_f$ of 0.8–0.9 while cholylglycine is less mobile. Solvent system III has been particularly useful for the iodinated product which has an $R_f$ significantly greater than unlabelled cholylglycylhistamine (0.72 versus 0.64). It gives a clear separation of cholylglycyl-$^{125}$I-histamine from cholylglycylhistamine. Solvent systems IV and V are useful to distinguish cholylglycylhistamine from free histamine. In systems II to V, anionic bile salts are immobile.

TABLE II

| REAGENT | PARTS BY VOLUME | | | | |
|---|---|---|---|---|---|
| | I | II | III | IV | V |
| Ethyl acetate | 40 | 50 | 50 | 55 | 55 |
| Benzene | 40 | — | 25 | — | — |
| Methanol | 10 | 40 | 25 | 35 | 35 |
| Acetic Acid | 10 | — | — | — | — |
| NH$_3$ | — | 10 | — | 10 | — |
| Triethylamine | — | — | 10 | — | — |
| Pyridine | — | — | — | — | 10 |

The synthesis, iodination, separation and purification procedures described above for cholylglycylhistamine and its radioiodination product may obviously be adapted to analogous compounds.

EXAMPLE 4

Preparation of Immunogen 6.3 mg of cholylglycine was dissolved in 1.5 ml of 0.1 M sodium carbonate buffer pH 7.0 containing 3.0 mg bovine serum albumin. 6.0 mg EDC was added to the solution and stirred for 18 hours at 4° C. 10$^6$ CPM of $^3$H cholylglycine was included in the incubation mixture to provide a measurement of coupling efficiency. Non-coupled cholylglycine and other reaction products were removed by dialysis against 2 changes of the same carbonate buffer. An aliquot of the BSA-cholylglycine conjugate was counted in a Beckman LS-133 liquid scintillation counter using Redi-solv IV. The average incorporation of the $^3$H-cholylglycine tracer was 4%.

EXAMPLE 5

Schedule of Immunization

Young adult male New Zealand white rabbits were immunized at multiple sites on the back at bi-weekly intervals using 1.0 ml of BSA-cholylglycine conjugate (50 μg) emulsified with an equal volume of Freund's adjuvant. Serum was harvested every 2 weeks beginning one month after the initial immunization.

EXAMPLE 6

Radioimmunoassay Procedure

The radioimmunoassay was similar to that reported by Simmonds et al in "Gastroenterology," Vol. 65, pp. 705–11 (1973). 1 mg bovine gamma globulin was included in each tube. Composition of a representative tube was 1 mg bovine gamma globulin, 10μ Moles phosphate buffer pH 7.4, 2000–3000 CPM of cholylglycyl-$^{125}$I-histamine, appropriately diluted antibody (rabbit serum) and an appropriate quantity of the serum being assayed (usually 10 μl) or cholylglycine standard and 10 μl of bile acid-free serum prepared according to Simmonds et al in a final volume of 1 ml. The reaction mixture was incubated overnight at 4° C. or at 42° C. for 45 minutes followed by 90 minutes at 4° C. Antibody bound cholylglycyl-$^{125}$I-histamine (bound) was separated from unbound bile salt (free) by Dextran coated charcoal prepared as follows: 5 gm Norit A activated neutral charcoal was washed 3 times with 100 ml of 10 mM PO$_4$ buffer pH 7.4 by gravity sedimentation. The washed Norit A charcoal suspended in 100 ml of 10 mM PO$_4$ buffer was added to 100 ml of 0.5% Dextran T-70 in 10 mM PO$_4$ buffer. The mixture was stirred for 5 minutes and allowed to sit at 4° C. for at least 3 hours before use. Prior to use the Dextran coated charcoal was diluted with an additional 300 ml 10 mM phosphate buffer pH 7.4 (as above described). The Dextran coated charcoal can be stored at 4° C. for a prolonged period. 0.5 ml of this solution was added to the assay tubes, vortexed, and incubated for 5 minutes at 4° C., and centrifuged at 1200 g×5 min. The supernate (bound) was decanted into another tube and both the charcoal (free) and supernate (bound) tubes were counted in a γ-spectrometer (Elscint). Results were expressed as the bound/free (B/F) ratio. A standard curve was constructed and unknowns were quantitated from a standard curve run with each assay.

Antibody Titer Curves

Figure 3:
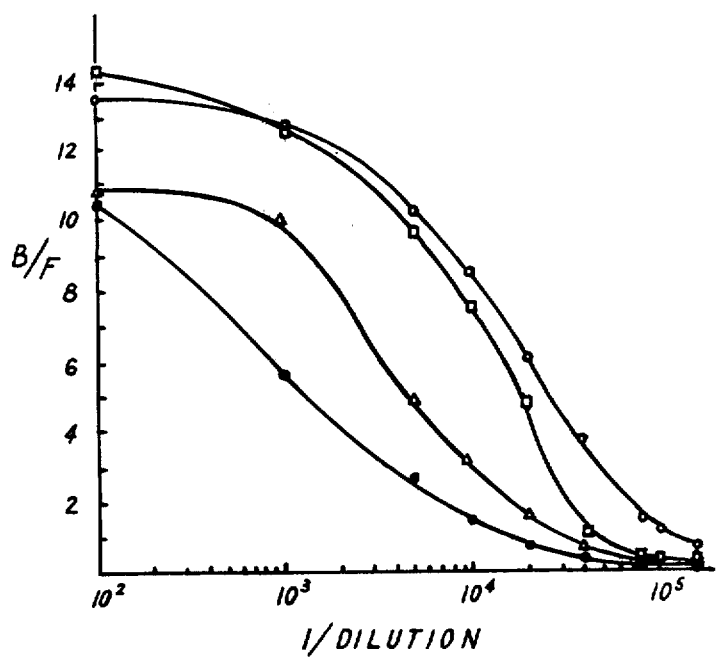
FIG. 3 shows the antibody titer curves for four antibodies, constructed according to the radioimmunoassay procedure of Example 6.

Antibodies from six different rabbits were produced and tested. FIG. 3 shows antibody titer curves for four of these antibodies using approximately 3000 CPM of cholylglycyl-$^{125}$I-histamine. At the smallest dilution used (1:100), the antibodies gave initial B/F values of 10.5 to 14.2. The value of 14.2 corresponds to binding 93% of the tracer. The antibody I have designated Ab 927, using $^3$H-cholylglycine, gives a B/F of 1.0 at 1:500 final dilution. The titer of this antibody, the curve for which is drawn through points represented as unblocked circles, increased to 1:80,000 using Ab 927 and approximately 2500–3000 CPM of cholylglycyl-$^{125}$I-histamine. Non-specific binding (the CPM which appear in the supernate when antibody is not included) is consistently 2–4% and remains unchanged as long as 6 months after iodination.

Specificity of Tracer and Antibody

Figure 4:
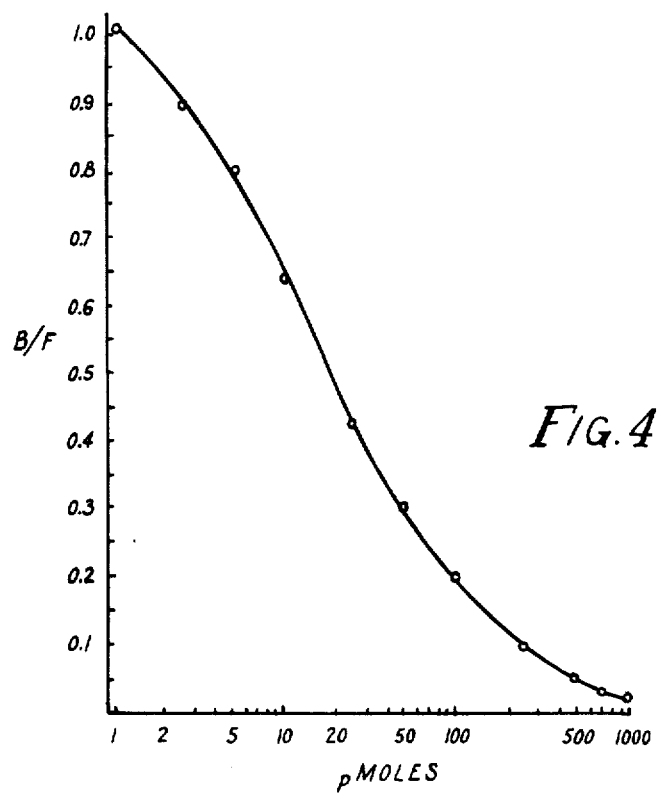
FIG. 4 shows a displacement curve obtained using chlolyltaurine, as described in Example 6.

FIG. 4 shows a displacement curve obtained using cholyltaurine. Displacement was most sensitive to cholyglycylhistamine which required approximately 10-fold less than other bile salts. Table III gives cross reactivities for various conjugated and unconjugated bile salts and other non-bile salt steroids. This table was constructed using additions of 100 pMoles of each bile salt or 1000 pMoles of the non-bile salt steroids except cholesterol 100,000 pMoles of which were added. Polyethylene glycol (PEG) and charcoal, in separate procedures, were used to separate the bound and free fractions. A cholyltaurine equivalent was assigned by comparison of the B/F on a cholyltaurine standard curve. The % cross-reactivity was taken as the ratio, cholyltaurine equivalent/pMoles actually added.

TABLE III

| Bile Salts | % Activity PEG | % Activity Charcoal | Non-Bile Salt Steroids | % Activity (PEG and Charcoal) |
|---|---|---|---|---|
| Cholyltaurine | 100 | 100 | Cholesterol | 0 |
| Cholylglycine | 84 | 33 | Estriol | 0 |
| Cholic acid | 33 | 1.7 | Cortisol | 0 |
| Chenodeoxycholytaurine | 27 | 3.5 | Testosterone | 0 |
|  |  |  | Digoxin | 0 |
| Chenodeoxycholylglycine | 92 | 26 |  |  |
| Chenodeoxycholic acid | 33 | 1.3 |  |  |
| Deoxycholylglycine | 28 | <0.5 |  |  |
| Deoxycholic acid | 10 | <0.5 |  |  |
| Lithocholic acid | 2 | <0.5 |  |  |

From among the naturally occurring bile salts, the assay was most sensitive to cholyltaurine which was given 100% activity. The assay was somewhat less sensitive to cholylglycine (84%) and chenodeoxycholylglycine (92%). The assay was less sensitive to the unconjugated bile salts, particularly lithocholate (2%).

The assay was found to be specific for bile salts in that representative estrogenic, androgenic, and adrenal steroids did not cross-react. The concentrations used are adequate to cover both physiologic and pathologic conditions. In addition, digoxin and cholesterol did not cross-react.

Figure 5:
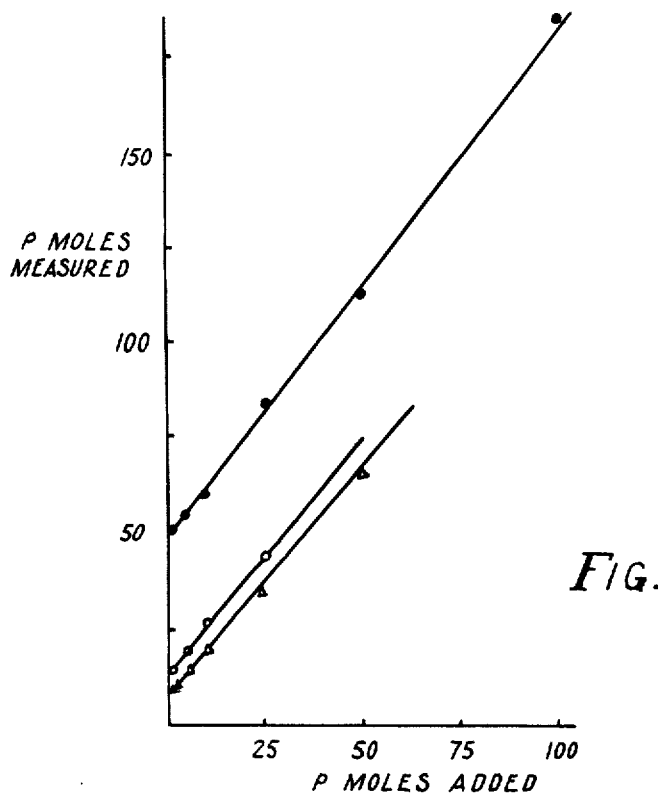
FIG. 5 shows results obtained by the recoveries of cholylglycine added to serum in a validation procedure described in Example 6.

Application of Cholylglycyl-$^{125}$I-histamine to Measurement of Serum Concentrations:

This assay was validated by recoveries of cholylglycine added to serum; for these studies a cholylglycine standard curve was used. FIG. 5 shows the results from addition of cholylglycine to serum of two patients with bile salt concentrations which were within the normal range and from one patient whose serum levels were considerably above normal. The additions used in the normal subjects started within the normal range and extended to elevated levels. In the elevated serum, additions were within the range of that serum and extended to much higher levels. As plotted in FIG. 5, the y-intercept is the level measured in that serum without addition. Recoveries were 120, 123 and 133% in these three sera. Intra-assay variability was tested by 10 separate determinations on two of these sera. Mean±SE were 55.2±1.25 and 9.03±0.43 p Moles per assay tube.

Figure 6:
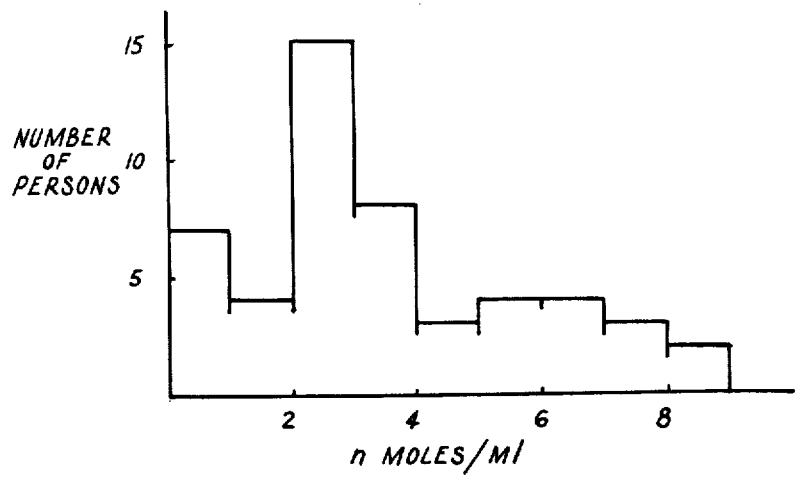
FIG. 6 shows the results of a study involving measurements of serum bile salts in a group of individuals who had no recognized disease, as explained in Example 6.

This iodinated bile salt derivative was used to measure serum bile salts in a group of individuals who had no recognized disease. FIG. 6 shows the results of these studies. The serum bile salt concentration in 50 normal individuals using Ab 927 and cholyglycyl-$^{125}$I-histamine was 3.5±2.2 (SD) nMoles/ml.

The use of the radioiodinated compounds of the present invention in physiological studies is demonstrated by the following illustrative examples.

EXAMPLE 7

Blood Clearance Study

Figure 7:
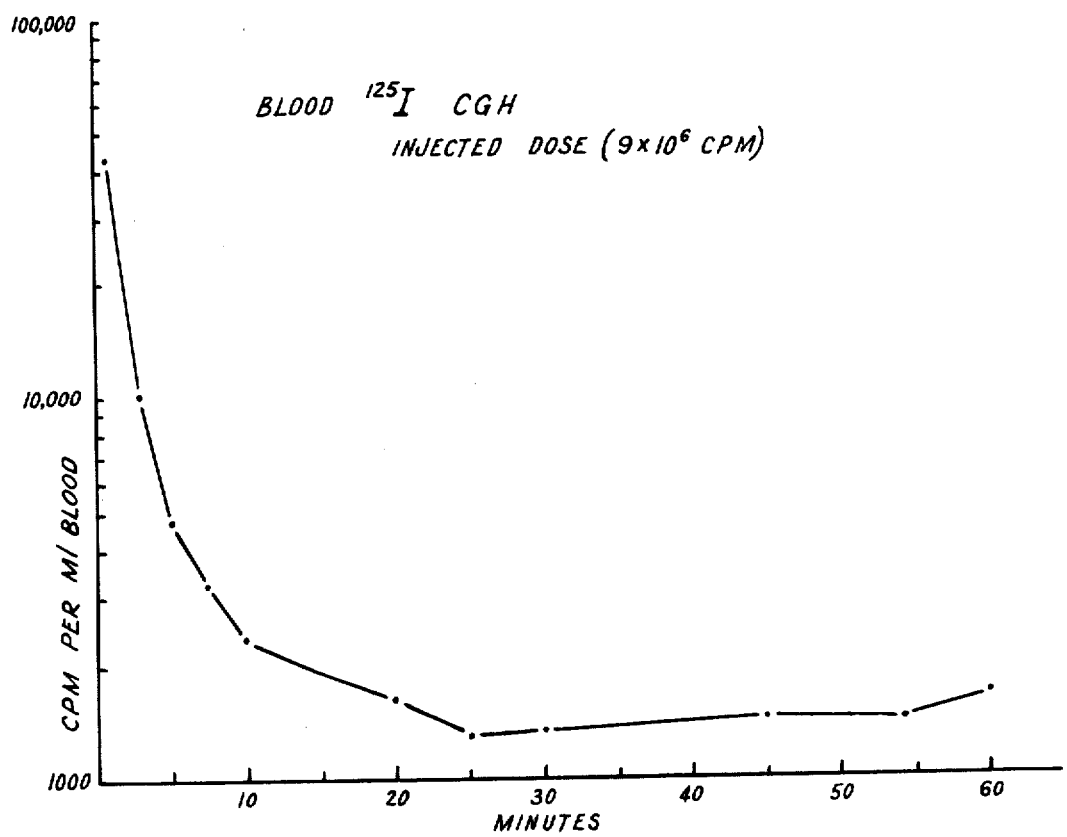
FIG. 7 is a curve illustrating the disappearance of $^{125}I$-CGH after injection in rabbits, as described in Example 7.

Blood clearance of the $^{125}$I bile salt in rabbits injected (ear vein) with 6 µCi $^{125}$I-CGH was measured. The graph, FIG. 7, shows the disappearance curve. The $t_{\frac{1}{2}}$ is about 3.0 minutes. At the end of the experiment gallbladder bile/blood concentration of $^{125}$I-CGH was 150.

EXAMPLE 8

Organ Distribution Study

To assess organ distribution of $^{125}$I-CGH, rats were injected in the tail vein and sacrificed 60 minutes later. The table below is the percent of the dose found in various organs. It is important that 80–90% of the radioactivity had been excreted by the liver and was found in the jejunum and ileum.

TABLE IV

| Liver | 2.1% | Jejunum | 9.0% |
|---|---|---|---|
| Spleen | 0.04% | Ileum | 82.6% |
| Stomach | 1.3% | Other organs | 2.06% |
| Duodenum | 2.9% |  |  |

Figure 8:
FIG. 8 is a superimposition photograph of a mouse injected with $^{125}I$-CGH and its hepatic scintigram as described in Example 8.

FIG. 8 is a superimposition photograph of a mouse injected with $^{125}$I-CGH and its hepatic scintigram. The liver is prominently displayed with some radioactivity appearing in the small intestine.

As seen from the foregoing, use of the bile salt derivatives of the present invention, in particular, cholylglycyl-$^{125}$I-histamine, has enabled conversion from liquid scintillation counting to use of a γ-spectrometer. The antibody titers have uniformly increased by 50–500 fold but sensitivity has not shown a corresponding increase. This is most likely based on the greater affinity of cholylglycylhistamine. Despite the greater affinity of cholylglycylhistamine, FIG. 3 and Table III show that sensitivity for primary conjugated bile salts remains in the clinically and experimentally useful range of 1 to 500 pMoles/assay tube.

The above described immunoassay using cholylglycylhistamine used an antibody developed using the parent conjugated bile salt, cholylglycine. The antibody and $^{125}$I-CGH maintain a specificity toward the conjugated bile salts, particularly cholate and chenodeoxycholate conjugates. The other bile salt derivatives are applicable with antibodies developed against their parent bile salts; for example, lithocholylglycylhistamine with antibodies developed using lithocholylglycine, and cholylhistamine with antibodies developed using cholic acid. Thus a family of immunoassays can use the appropriate iodinatable derivative of each bile salt with antibodies developed against its parent bile salt, e.g.:

| Label (tracer) | Antibody Developed Against |
|---|---|
| Cholylglycylhistamine | Cholyglycine |
| Lithocholylhistamine | Lithocholic acid |
| Cholyltyrosine | Cholic acid |
| Deoxycholylglycylhistidine | Deoxycholylglycine |

The same scheme is applicable to each bile salt and each included iodinatable derivative.

The radioimmunoassay described here is not monospecific; Ab 927 and cholylglycyl-$^{125}$I-histamine measure predominantly the primary conjugated bile salts. Other antibodies produced against cholylglycine-bovine serum albumin have had specificities different from those reported here. The specificities also differ from those found using less dilute antibody (1:500) and $^3$H cholylglycine as tracer. Defining the contribution of the tracer and the antibody to assay specificity will depend on detailed testing of a family of iodinated derivatives with multiple antibodies. At this time there seems little reason to favor a mono-specific assay over a system which quantitates several bile salts. As new antibodies are used, cross reactivities may be assessed as has been shown above for Ab 927.

The specificity of the tracer may be altered by using other iodinatable derivatives such as the histidine, histidine methyl ester, tyrosine, tyrosine methyl ester, or tyramine (tyrosamine). Specificities may also be altered by conjugation at a 3-α-hydroxyl group instead of the bile salt or glycine carboxyl group or by iodination of unsaturated bile salts.

EXAMPLES 9 AND 10

Preparation and Iodination of Cholylglycyltyrosamine and Cholylglycyltyrosine

Figure 9:
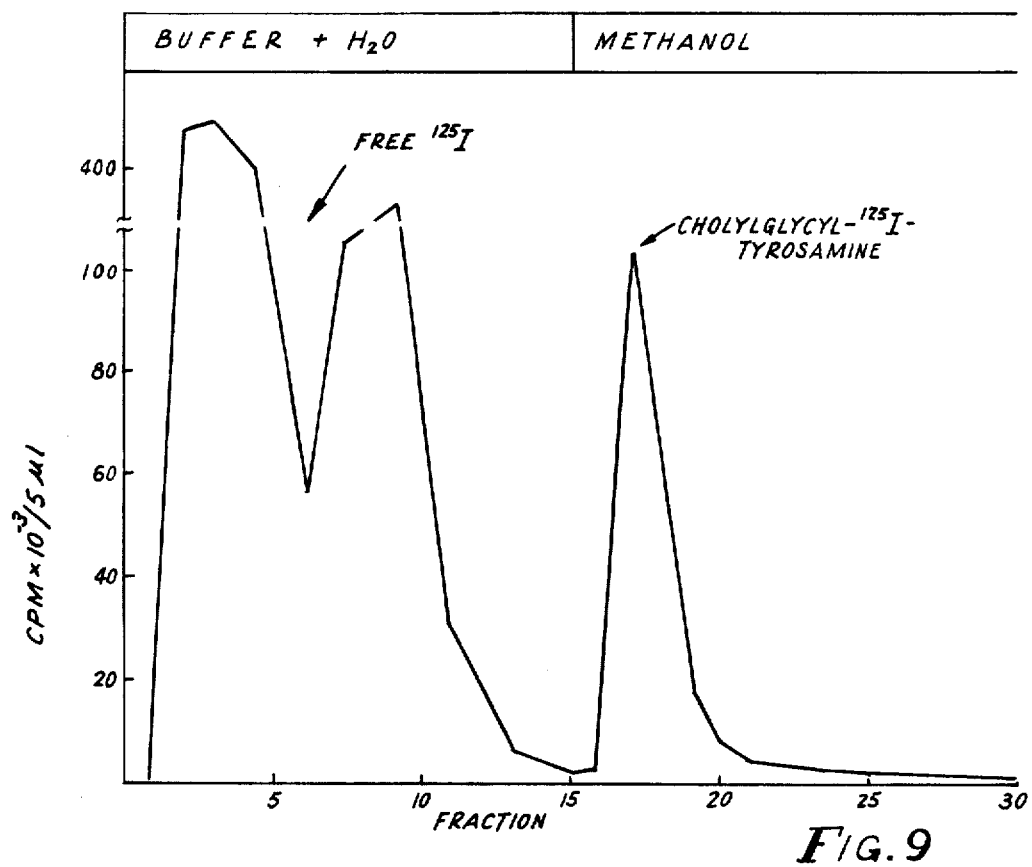
FIGS. 9 and 10 are the elution profiles obtained in the preparation of cholylglycyl-$^{125}I$-tyrosamine and cholylglycyl-$^{125}I$-tyrosine, as explained in Examples 9 and 10.
Figure 10:
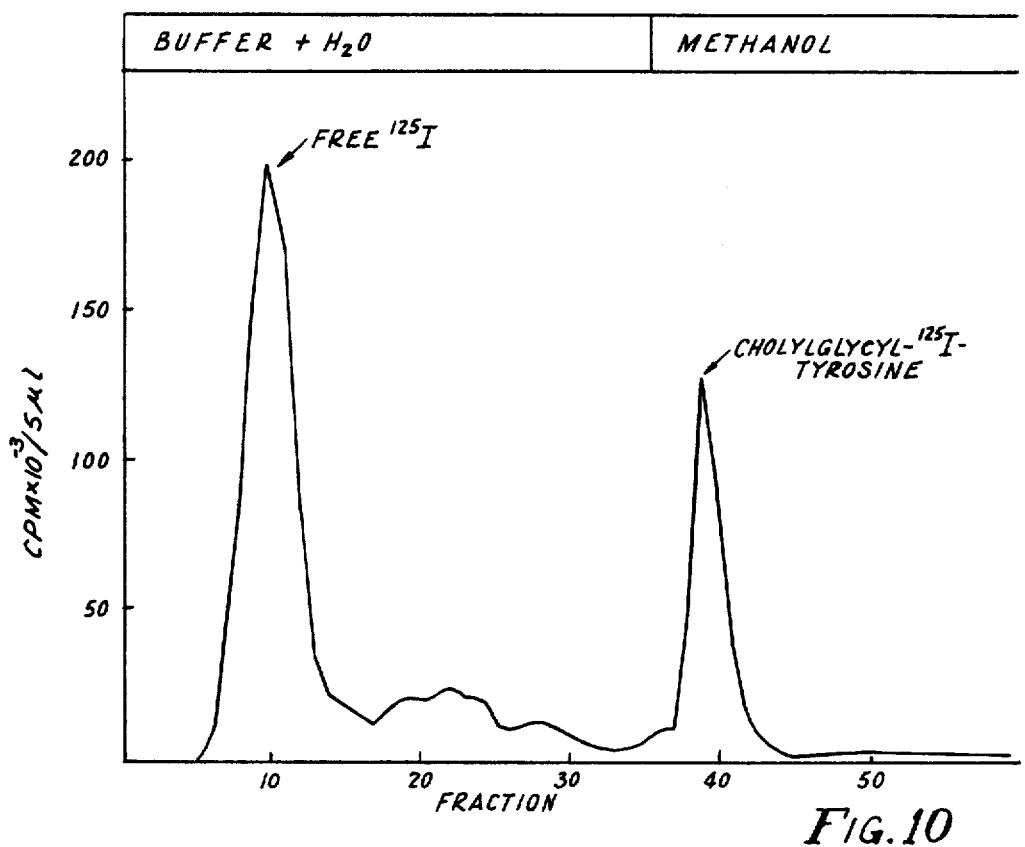

Using only 1 nMole of the bile salt, both cholylglycyl-$^{125}$I-tyrosamine and cholylglycyl-$^{125}$I-tyrosine were prepared and purified through the Amberlite resin, using the procedures corresponding to those of Examples 1 and 2, above. FIGS. 9 and 10, respectively, are the elution profiles obtained.

Numerous modifications and variations of the present invention are possible in light of the above teachings and, accordingly, within the scope of the appended claims the invention may be practiced in a manner other than as particularly described.

I claim:

1. A process for separating an iodinated cationic bile acid conjugate, said iodinated conjugate being a bile acid or an amino acid or diamine amide-bonded conjugate thereof linked directly or indirectly to a group containing iodine, from a solution also containing the corresponding uniodinated conjugate, comprising applying said solution to the origin of a thin layer chromatography sheet, developing a chromatogram by means of a solvent containing a nitrogen base, whereby a band of iodinated conjugate migrates to a position beyond a band of uniodinated conjugate, and removing said iodinated conjugate; said bile acid being selected from the group consisting of cholic acid, chenodeoxycholic acid, deoxycholic acid and lithocholic acid, and said group containing iodine being selected from the group consisting of tyrosine, tyrosine esters, histidine, histidine esters, tyramine, histamine, phenylpropionic acid, phenylalanine, phenylalanine esters, tryptophane and tryptophane esters.

2. The process of claim 1 wherein said solvent contains also a lower alkyl ester of a lower alkanoic acid, said ester having up to 8 carbon atoms.

3. The process of claim 2, wherein the iodine is $^{123}$I, $^{125}$I or $^{131}$I.

4. The process of claim 3 wherein said thin layer chromatography sheet is a silica gel chromatography sheet.

5. The process of claim 4 wherein said solvent is caused to ascend said chromatography sheet and said band of iodinated conjugate migrates to a position above said band of uniodinated conjugate.

6. The process of claim 3, wherein said nitrogen base is selected from the group consisting of primary, secondary and tertiary alkylamines and arylamines, heterocyclic amines, ammonium hydroxide and hydroxylamine.

7. The process of claim 4, wherein said nitrogen base is selected from the group consisting of trimethylamine, triethylamine, tripropylamine, tributylamine, dicyclohexylamine, aniline, pyridine, ammonium hydroxide and hydroxylamine.

8. The process of claim 1, wherein said lower alkyl ester of a lower alkanoic acid is ethyl acetate.

9. The process of claim 1, wherein said solvent contains benzene.

10. The process of claim 1, wherein said solvent contains a lower alkanol.

11. The process of claim 10, wherein said solvent contains about 25 parts by volume of said alkanol, about 10 parts by volume nitrogen base and about 25 to 50 parts by volume each of ethyl acetate and benzene, the amount by volume of the latter two components totaling about 75 parts.

12. The process of claim 3, wherein said conjugated bile acid is cholylglycylhistamine and said solvent contains 50 parts by volume ethyl acetate, 25 parts by volume benzene, 25 parts by volume methanol and 10 parts by volume triethylamine.

13. The process of claim 3, wherein said mixture of iodinated and uniodinated cationic bile and conjugate is that obtained by (1) reacting said cationic bile acid conjugate with an iodinating mixture comprising sodium iodide and chloramine-T and (2) separating a said mixture of iodinated and uniodinated conjugate from the reaction mixture.

14. The process of claim 13, wherein said mixture of iodinated and uniodinated conjugate is separated from the reaction mixture by selectively adsorbing it on a resin and eluting the resin with a solvent.

15. The process of claim 14, wherein said mixture is a mixture of iodinated and uniodinated cholylglycyl histamine, said resin has a polystyrene backbone and said solvent is methanol or ethanol.

16. A process for separating an iodinated anionic bile acid conjugate, said iodinated conjugate being a bile acid or an amino acid or diamine amide-bonded conjugate thereof linked directly or indirectly to a group containing iodine, from a solution also containing the corresponding uniodinated conjugate, comprising applying said solution to the origin of a thin-layer chromatography sheet, developing a chromatogram by means of a solvent containing a weak acid, whereby a band of uniodinated conjugate migrates to a position beyond a band of iodinated conjugate and removing said iodinated conjugate; said bile acid being selected from the group consisting of cholic acid, chenodeoxycholic acid, deoxycholic acid and lithocholic acid, and said group containing iodine being selected from the group consisting of tyrosine, tyrosine esters, histidine, histidine esters, tyramine, histamine, phenylpropionic acid, phenylalanine, phenylalanine esters, tryptophane and tryptophane esters.

17. The process of claim 16, wherein the iodine is $^{123}$I, $^{125}$I or $^{131}$I, said thin layer chromatography sheet is a silica gel chromatography sheet and said solvent contains 40% ethyl acetate, 40% benzene, 10% methanol and 10% acetic acid, by volume.

18. The process of claim 6, wherein the solvent contains 5-20% nitrogen base, 20-80% lower alkyl ester of alkanoic acid and 0-75% of a component selected from the group consisting of benzene and its lower homologues, lower alkanols, lower alkanones, di-lower alkyl ethers wherein the alkyl moieties may be the same or different, and mixtures thereof.

19. The process of claim 7, wherein the solvent contains 5-20% nitrogen base, 20-80% lower alkyl ester of alkanoic acid and 0-75% of a component selected from the group consisting of benzene and its lower homologues, lower alkanols, lower alkanones, di-lower alkyl ethers wherein the alkyl moieties may be the same or different, and mixtures thereof.

* * * * *